United States Patent [19]
Briggs, III et al.

[11] Patent Number: 5,641,464
[45] Date of Patent: Jun. 24, 1997

[54] STETHOSCOPE CLEANSING DEVICE AND METHOD

[75] Inventors: Stephen W. Briggs, III; John D. Calebaugh, both of Orangevale, Calif.

[73] Assignee: B & B Medical Technologies, Inc., Orangevale, Calif.

[21] Appl. No.: 565,843

[22] Filed: Dec. 1, 1995

[51] Int. Cl.[6] .................................................. A61L 2/18
[52] U.S. Cl. ........................... 422/300; 239/274; 134/200
[58] Field of Search ............................. 422/292, 300; 134/198, 200; 239/274; 222/183, 505

[56] References Cited

U.S. PATENT DOCUMENTS

| | | | |
|---|---|---|---|
| 2,046,606 | 7/1936 | Borba | 422/300 X |
| 3,286,883 | 11/1966 | Takiff | 239/274 X |
| 3,292,993 | 12/1966 | Musso | 422/300 |
| 3,342,544 | 9/1967 | Curiel | 422/300 |
| 3,943,951 | 3/1976 | Spotz | 134/200 X |
| 4,997,629 | 3/1991 | Marchand et al. | 422/300 |
| 5,074,322 | 12/1991 | Jaw | 422/300 X |
| 5,132,518 | 7/1992 | Solacoff | 219/385 |
| 5,168,888 | 12/1992 | Altwasser | 134/200 X |
| 5,486,659 | 1/1996 | Rosenbush | 181/131 |

*Primary Examiner*—Robert J. Warden
*Assistant Examiner*—E. Leigh Dawson
*Attorney, Agent, or Firm*—Donald E. Nist

[57] ABSTRACT

The improved device is used in the present method for cleansing the head of a stethoscope with an antimicrobial spray liquid. The device includes a housing which defines a generally central cavity in which an aerosol spray cannister is releasably disposed in a bracket. The housing is closed but is openable in order to replace the cannister, as needed. The housing includes an openable port, such as an elastomeric iris, through which the head of a stethoscope, in accordance with the present method, is inserted for cleansing in the cavity. The cannister has a spray nozzle which is activatable by a trigger in the form of a lever secured in the cavity and extending out of the housing. The lever is disposed above the nozzle and can be manually moved from outside the housing to depress the nozzle and cause antimicrobial spray to be aerosol dispensed from the cannister in a path in the cavity which the stethoscope head intersects. The housing cavity can include a drip plate and one or more baffles to prevent the spray from exiting through the stethoscope port and to direct the spray to a drain area in the housing. The device can be suspended from a wall by screws or the like. After the stethoscope head is sprayed in the cavity, it is withdrawn therefrom and wiped free of spray with a clean cloth or the like. The device and method are simple, efficient and inexpensive.

2 Claims, 2 Drawing Sheets

5,641,464

1

STETHOSCOPE CLEANSING DEVICE AND METHOD

BACKGROUND OF THE INVENTION

1. Field of the Invention

The present invention generally relates to cleansing means and more particularly to an improved device and method for cleansing the head of a stethoscope.

2. Prior Art

Stethoscopes are in constant use by physicians, nurses, respiratory care practitioners and other clinical personnel in hospitals, medical offices, nursing care facilities and in other similar facilities for monitoring heart beats, breath sounds and blood pressures. As such, stethoscopes are a potential source of transmission of infections from one patient to another and between medical personnel and patients.

Nosocomial or hospital acquired infections are a leading cause of death of seriously ill patients. In 1958 over 50% of life-threatening infections in patients were acquired while the patients were in the hospital and 14% of such infections resulted in death. Although the acquisition of life-threatening infections by patients in hospitals is currently only about 5%, in many instances the virulence and seriousness of such infections has increased, especially since the advent of HIV-positive conditions, AIDS, Hepatitis A,B and C and the like.

Not only are hospital-acquired diseases potentially disasterous for patients, they can also be the focus of expensive lawsuits for medical malpractice. Therefore, modern medical personnel are acutely aware of the dangers of infection and take steps to prevent their transmission. However, such steps as are normally taken with respect to cleansing stethoscopes are relatively primitive and ineffective. Prepackaged isopropyl alcohol swabs are frequently used to wipe off the head of a stethoscope. However, the swabs are relatively expensive. Of more importance, isopropyl alcohol only has a limited bactericidal effect. It does not kill a large number of types of bacteria. Therefore, the potential for the acquisition of a disease via the stethoscope head remains.

Although the Nursing Risk Management and Education Department of most hospitals attempts to remind each clinician to hand wash prior to performing any procedure on a patient in order to reduce cross-contamination, monitoring of compliance with this instruction is impossible. After a stethoscope comes into direct contact with a patient, it now bears on its head whatever patient bacteria, flora and other contaminants that the patient has. The hazard for the clinician and any other patients to which the stethoscope head is applied thereafter is great, especially in view of the advent of the previously mentioned HIV virus and Hepatitis B, among other serious diseases.

There remains a need for an improved device which can conveniently, inexpensively and rapidly cleanse the head of a stethoscope so that it is essentially disinfected and reduces the potential source of transmission of disease. There also remains a need for a method employing such device for the cleansing procedure.

SUMMARY OF THE INVENTION

The improved stethoscope sterilizing device of the present invention satisfies all the foregoing needs. The device is substantially as set forth in the ABSTRACT OF THE DISCLOSURE.

Thus, the device of the present invention is simple, inexpensive, efficient and durable. It is used with the present

2 claimed method for conveniently cleansing the head of a stethoscope in a rapid and thorough manner.

The device comprises a closed but openable housing having a plurality of interconnected sidewalls, rear and front, top and bottom to define a generally central space in which is releasably disposed an aerosol cannister holding a sprayable disinfecting liquid. The liquid preferably is totally bactericidal and germicidal and therefore capable of ridding the stethoscope head of all biological contamination. The cannister is disposed in a bracket connected to one or more walls in the space in the housing.

The housing also includes a normally closed but openable port through which the head of the stethoscope is fed into the housing space and into contact with a spray of liquid from the cannister. The port preferably is in the form of an elastomeric iris which protects the clinician from the disinfecting spray.

The cannister has a spray nozzle spring biased into the "OFF" position but which can be depressed into the "ON" position by a trigger in the form of a lever connected to the interior of the housing and disposed in the generally central space in close proximity to the nozzle of the cannister. The lever extends out of the housing and is manually moveable to depress the nozzle and thus cause the cannister to spray the disinfecting liquid therefrom and onto the head of the stethoscope in the central space.

The device preferably is also provided with one or more baffles to shield the user against the spray and to direct the spray in the central space to a drip plate and ultimately to a drainage area.

The method of the present invention involves introducing the stethoscope head into the central space in the housing, activating the spray to disinfect the head and then shutting off the spray and removing the stethoscope head from the housing and wiping it dry with a clean cloth or the like.

The housing has a removable front and/or top or the like for access to the cannister to replace it and to clean the central space when needed. Screws may be provided for hanging the housing on a wall adjacent a wash bowl or the like. Further features of the improved device and method of the present invention are set forth in the following detailed description and accompanying drawings.

DETAILED DESCRIPTION OF THE INVENTION

FIGS. 1–3.

Figure 1:
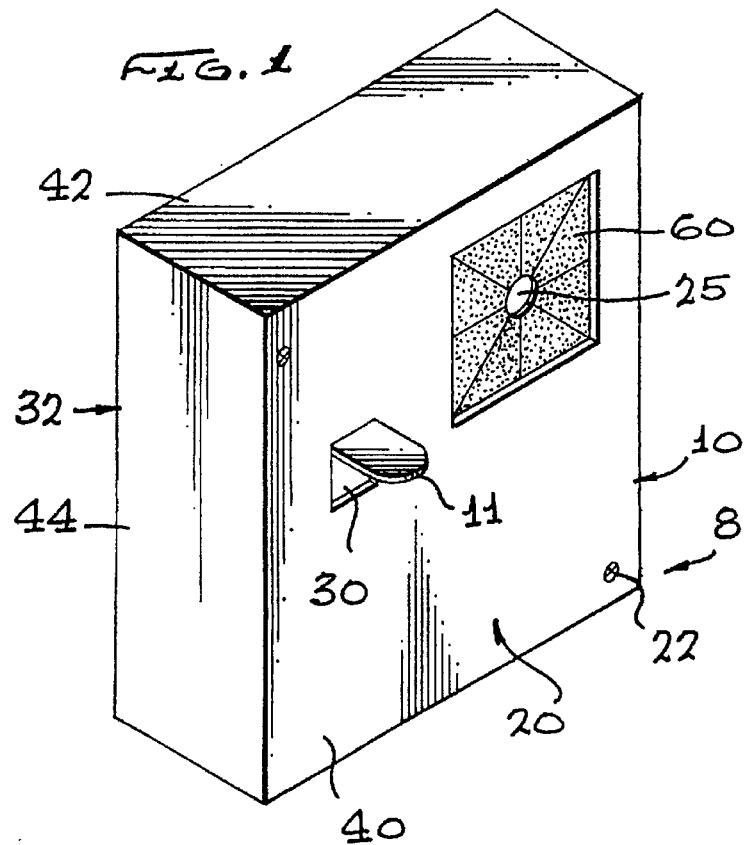
FIG. 1 is a schematic front and side perspective view of a preferred embodiment of the improved stethoscope head disinfecting device of the present invention.
Figure 2:
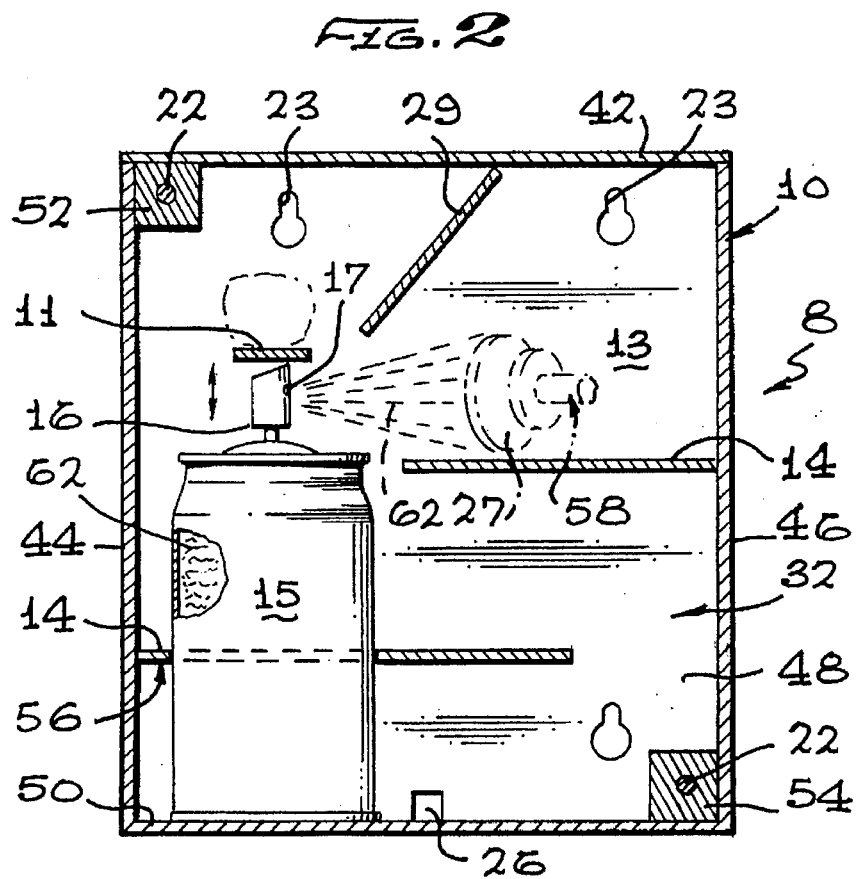
FIG. 2 is a schematic vertical cross-section of the device of FIG. 1, showing partly in phantom outline the aerosol spray cannister of the device spraying disinfecting liquid on a stethoscope head while the activating lever of the device is depressed with a thumb; and, FIG. 3 is a schematic exploded side perspective view of the device of FIG. 1, illustrating the internal construction of the housing of the device.
Figure 3:
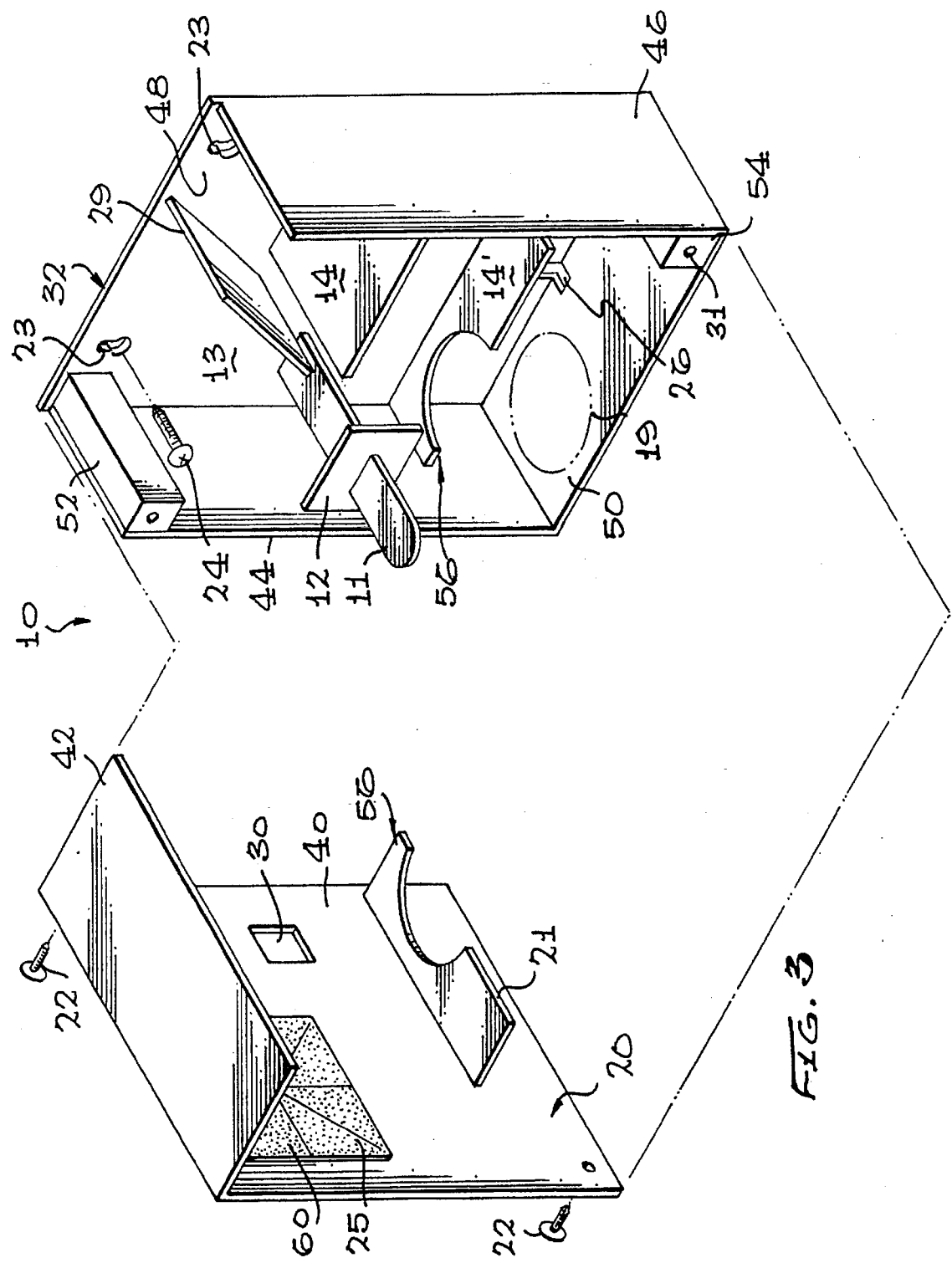

Now referring more particularly to FIGS. 1–3 of the drawings, a preferred embodiment of the improved device of the present invention is schematically depicted therein. Thus, device 8 is shown which includes housing 10. Housing 10 comprises, as indicated in FIG. 3, a front cover unit 20 which includes a front plate 40 and top plate 42 (inverted L-shaped in side elevation) secured releasably to a rear unit 32, as by screws 22. Rear unit 32 comprises spaced vertical sidewalls 44 and 46, vertical rear wall 48 and horizontal bottom wall 50 interconnected to form a box open at the front and top. Units 20 and 32 when connected together form housing 10 and define a generally central internal space or spray chamber 13.

In chamber 13 are mounted anchoring blocks 52 and 54 for screws 22 and an elongated blade-shaped trigger in the form of a lever 11. Lever 11 is secured at its rear end to rear wall 48 and extends horizontally forwardly therefrom through space 13 and out an exit port 30 in front plate 40. Lever 11 bears a vertical shield 12 which is positioned just inside front plate 40 in space, 13 to prevent aerosol spray from exiting space 13 through port 30. An angled baffle 29 is secured to rear wall 48 above lever 11 in space 13. Screw holes 31 are in blocks 52 and 54.

Space 13 also contains a horizontal drip plate 14 secured to rear wall 48 and sidewall 46, and the two halves 21 and 14 of a bracket 56 releasably holding an aerosol spray cannister 15 (FIG. 2) which rests on spot 19 on bottom wall 50 in space 13. Cannister 15 forms part of device 8.

An opening 26 is provided in housing 10, specifically at the rear end of bottom wall 50 and the lower end of rear wall 48 to act as an aerosol exhaust port. Rear wall 48 also defines a spaced pair of openings 23 through which screws 24 can releasably secure housing 10 to a wall (not shown) in a clean-up area for clinicians or the like.

Front plate 40 defines a port 25 through which the head 27 of a stethoscope 58 can be inserted into space 13, as shown in FIG. 2. Port 25 may be provided with a flexible resilient closeable X-shaped or iris-shaped diaphragm 60 so that when head 27 is inserted into space 13, diaphragm 60 closes around tube 28 of stethoscope 58, sealing plate 40 from egress of aerosol spray from cannister 15.

In this regard, cannister 15 is filled with a disinfecting liquid 62 and a propellant (not shown), the latter of which forces liquid 62 as an aerosol spray from cannister 15 when the spring biased nozzle 16 at the upper end of cannister 15 is depressed. Nozzle 16 is positioned immediately below lever 11 in space 13 so that when the clinician presses the free end (the end projecting forwardly out of housing 10) of lever 11 down, it depresses nozzle 16 and allows disinfecting liquid 62 to spray out of orifice 17 in nozzle 16.

Opening 25 is aligned relative to bracket 56 and nozzle 16 such that when stethoscope head 27 is in space 13, it is directly in the path of liquid 62 being sprayed from cannister 15, quickly and effectively disinfecting head 27.

Liquid 62 can be any suitable disinfecting sprayable liquid which has a disinfecting, or sterilizing or similar effect, for example, a bactericide, virucide, sporacide, germicide or the like. Quaternary ammonium compounds such as hexamethonium chloride, lauryl pyridinium chloride and octadecylmethylbenzyl ammonium chloride can be used. So also can other related cationic surface active compounds having the desired disinfecting activity. Other disinfecting liquids can also be used.

Housing 10 can be of any suitable size and shape. Preferably, it is relatively small and compact, for example, about 6 inches wide, 8 inches tall and 4 inches deep. It must merely be sufficient in size to accept a suitable cannister 15 of disinfecting liquid 62 and the head 27 of a stethoscope 58.

The method of the present invention utilizes the device of the present invention for disinfecting stethoscope heads. In accordance with the method, head 27 is first introduced into space 13, after which lever 11 is depressed so that liquid 62 is sprayed directly on head 27, disinfecting it, after which head 27 is withdrawn from space 13 and then wiped dry with a clean cloth, towel, tissue or the like.

As a specific example, housing 10 having the dimensions and components set forth above is used in the present method. Cannister 15 is filled with propellant and hexamethonium chloride, a disinfectant. Lever 11 is depressed after head 27 is in place, as shown in FIG. 2. A spray of the disinfecting liquid disinfects head 27. The spray is continued for about 2 seconds, after which the depressing force on lever 11 is removed, so that lever 11 swings up away from nozzle 16 and the spraying terminates. Thereafter, head 27 is withdrawn by tube 18 from space 13 and wiped dry with a clean dry cotton patch, so that stethoscope 58 is now ready for reuse.

Various modifications, changes, alterations and additions can be made in the improved device of the present invention, its components and their parameters, and in the present method and in its steps and parameters. All such modifications, changes, alterations and additions as are within the scope of the appended claims form part of the present invention.

What is claimed is:

1. An improved device for cleansing a stethoscope, said device comprising, in combination:
  a) an openable, closed, rectangular aerosol canister support housing comprising flat interconnected walls, said walls comprising a front vertical wall, a rear vertical wall, two opposite side walls, a horizontal top wall and a horizontal bottom wall collectively defining a central cavity, said top wall and said front wall forming a unit releasably connected to the remainder of said housing for easy access to said central cavity, said rear wall including means for mounting said housing on a building wall;
  b) an aerosol support bracket mounted in said central cavity and connected to the interior surface of at least one of said rear wall, bottom wall and side walls;
  c) an aerosol canister releasably secured in said support bracket in said cavity and including an aerosol spray dispensing nozzle at the upper end thereof spring biased to the non-dispensing position, said canister containing sprayable antimicrobial liquid;
  d) a trigger comprising an elongated, horizontal movable blade having opposite front and rear ends, said rear end being secured to the inner surface of said rear wall, said front end extending out of an opening in said front wall of said housing, said blade being positioned above said nozzle but being depressible to cause said canister to spray;
  e) an access port having an iris with elastic memory in said front wall for introducing a stethoscope head into the path of spray from said aerosol canister when said trigger is activated;
  f) a baffle plate secured to the interior of said housing and extending into said central cavity above the level of said iris to direct said spray to said stethoscope head in said cavity; and,
  g) a spray drain hole in at least one of the rear end of said bottom wall and the bottom end of said rear wall.

2. The improved device of claim 1 wherein said canister liquid is at least one of bacteriostatic, bacteriocidal, germicidal, virucidal, sporicidal and fungicidal for disinfecting said stethoscope head.

\* \* \* \* \*